(12) United States Patent
Hoshide et al.

(10) Patent No.: US 8,486,021 B2
(45) Date of Patent: Jul. 16, 2013

(54) SYRINGE DRIVE UNIT

(75) Inventors: Kaoru Hoshide, Tokyo (JP); Hirokazu Tatsuzuki, Tokyo (JP); Takashi Ogata, Tokyo (JP)

(73) Assignee: THK Co., Ltd., Tokyo (JP)

( * ) Notice: Subject to any disclaimer, the term of this patent is extended or adjusted under 35 U.S.C. 154(b) by 27 days.

(21) Appl. No.: 13/147,131

(22) PCT Filed: Feb. 23, 2010

(86) PCT No.: PCT/JP2010/052723
§ 371 (c)(1),
(2), (4) Date: Jul. 29, 2011

(87) PCT Pub. No.: WO2010/110001
PCT Pub. Date: Sep. 30, 2010

(65) Prior Publication Data
US 2011/0301540 A1   Dec. 8, 2011

(30) Foreign Application Priority Data

Mar. 27, 2009 (JP) ................................. 2009-079765

(51) Int. Cl.
*A61M 37/00* (2006.01)
(52) U.S. Cl.
USPC ........................................................ 604/155
(58) Field of Classification Search
USPC .................. 604/68–72, 155, 181–243, 82–92
See application file for complete search history.

(56) References Cited

U.S. PATENT DOCUMENTS
2006/0079833 A1   4/2006   Kobayashi

FOREIGN PATENT DOCUMENTS

| JP | 2-103269 U | | 8/1990 |
|---|---|---|---|
| JP | 6-71904 U | | 10/1994 |
| JP | 11-182415 | * | 7/1999 |
| JP | 11-182415 A | | 7/1999 |
| JP | 2002-364526 A | | 12/2002 |

(Continued)

OTHER PUBLICATIONS

International Search Report of PCT/JP2010/052723, date of mailing May 18, 2010.

*Primary Examiner* — Nicholas Lucchesi
*Assistant Examiner* — Pritesh Patel
(74) *Attorney, Agent, or Firm* — Westerman, Hattori, Daniels & Adrian, LLP

(57) ABSTRACT

Provided is a syringe drive unit (1) which is capable of imparting a fine moving amount to a plunger pressing member (6) when a plunger is pushed into a syringe body using a feed screw mechanism, to thereby eject liquid medicine from the syringe body with high accuracy. The syringe drive unit (1) includes: a syringe holder (3) which is fixed to a front surface side of a base plate (2) and holds the syringe body; a guide rail (4) which is provided on a rear surface side of the base plate (2) along an axial-line direction of the syringe body; a slider (5) which is assembled to the guide rail (4) through intermediation of rolling elements; a plunger pressing member (6) which is fixed to the slider (5) and includes an arm portion (61) projecting from the rear surface side of the base plate (2) to the front surface side of the base plate (2), the arm portion (61) holding the plunger housed in the syringe body; a screw shaft (7) which is provided parallel to the guide rail (4) and has predetermined rotation imparted by a motor (9); and a nut member (8) for imparting a moving amount corresponding to a rotation amount of the screw shaft (7) to the plunger pressing member (6).

3 Claims, 7 Drawing Sheets

FOREIGN PATENT DOCUMENTS

| | | |
|---|---|---|
| JP | 2004-162560 A | 6/2004 |
| JP | 2004-338003 A | 12/2004 |
| JP | 2006-070868 A | 3/2006 |
| JP | 2007-077848 A | 3/2007 |

* cited by examiner

SYRINGE DRIVE UNIT

TECHNICAL FIELD

The present invention relates to a syringe drive unit to be used with a syringe mounted thereto at the time of ejecting liquid medicine loaded into the syringe at a predetermined flow rate.

BACKGROUND ART

Conventionally, as the syringe drive unit of this type, syringe drive units disclosed in JP 2006-070868 A (Patent Literature 1) and JP 2004-162560 A (Patent Literature 2) have been well known. Those syringe drive units each include a syringe holder for holding a syringe body, a plunger pressing member for pressing a plunger housed in the syringe body, and a feed screw mechanism for moving the plunger pressing member into an axial-line direction of the syringe body in accordance with rotation of a motor. When the motor is rotated, the plunger is pushed into the syringe body in accordance with a rotational amount thereof, and liquid medicine loaded into the syringe body is ejected from the syringe body in accordance with a pushing-in amount of the plunger.

In the syringe drive unit structured as described above, the liquid medicine in the syringe body is ejected in accordance with a moving amount of the plunger, and hence it is necessary to strictly control a moving amount of the plunger pressing member. The moving amount is controlled, for example, through what is called open loop control using a stepping motor as the motor, and what is called closed loop control performed while an actual moving amount of the plunger pressing member is grasped using measuring means such as a potentiometer.

CITATION LIST

Patent Literature

Patent Literature 1: JP 2006-070868 A
Patent Literature 2: JP 2004-162560 A

DISCLOSURE OF THE INVENTION

Problems to be Solved by the Invention

The plunger pressing member is propelled by the feed screw mechanism so as to press the plunger housed in the syringe body. In this case, a reaction force against a pressing force acts on the plunger pressing member, and a point of action of a propulsive force and a point of action of the pressing reaction force are separated from each other. As a result, a moment load acts on the plunger pressing member. In the conventional syringe drive units, the plunger pressing member is supported only by the feed screw mechanism, and a bearing capacity with respect to the moment load is small. Thus, even when the feed screw mechanism is driven with high accuracy, it is difficult to impart a fine moving amount to the plunger, which leads to difficulty in ejection of the liquid medicine from the syringe body with high accuracy.

Means for Solving the Problems

The present invention has been made in view of the above-mentioned problem, and it is therefore an object of the present invention to provide a syringe drive unit which is capable of firmly supporting, against a moment load, a plunger pressing member for holding a plunger, and imparting a finer moving amount to the plunger pressing member when the plunger is pushed into a syringe body using a feed screw mechanism, to thereby eject liquid medicine from the syringe body with high accuracy.

That is, the syringe drive unit of the present invention includes: a base plate; a syringe holder which is fixed to a front surface side of the base plate and holds a syringe body; a guide rail which is provided on a rear surface side of the base plate along an axial-line direction of the syringe body mounted to the syringe holder; a slider which is assembled to the guide rail through intermediation of a large number of rolling elements and movable along the guide rail; a plunger pressing member which is fixed to the slider and includes an arm portion projecting from the rear surface side of the base plate to the front surface side of the base plate, the arm portion holding a plunger housed in the syringe body; a screw shaft which is provided on the rear surface side of the base plate parallel to the guide rail and has predetermined rotation imparted by a motor; and a nut member which is threadedly engaged with the screw shaft to impart a moving amount corresponding to a rotation angle of the motor to the plunger pressing member.

Effects of the Invention

According to the present invention structured as described above, the plunger pressing member is fixed to the slider assembled to the guide rail through intermediation of a large number of balls, and is in a state of being bounded by the guide rail except in the axial-line direction of the syringe body. That is, the guide rail and the slider assembled thereto bear the moment load acting on the plunger pressing member, and the plunger pressing member is guided while maintaining a certain posture. Thus, the plunger pressing member can be moved in accurate correspondence with the rotation angle of the motor, with the result that liquid medicine can be extracted from the syringe body with high accuracy.

Further, a position at which the plunger is pressed by the plunger pressing member and a position at which the track rail for guiding the plunger pressing member is arranged are significantly close to each other so as to sandwich the base plate. Thus, the plunger pressing member can be firmly held against the pressing reaction force. Also in this regard, the moving amount of the plunger pressing member can accurately correspond to the rotation angle of the motor.

MODE FOR CARRYING OUT THE INVENTION

In the following, detailed description is made of a syringe drive unit according to the present invention with reference to the accompanying drawings.

Figure 1:
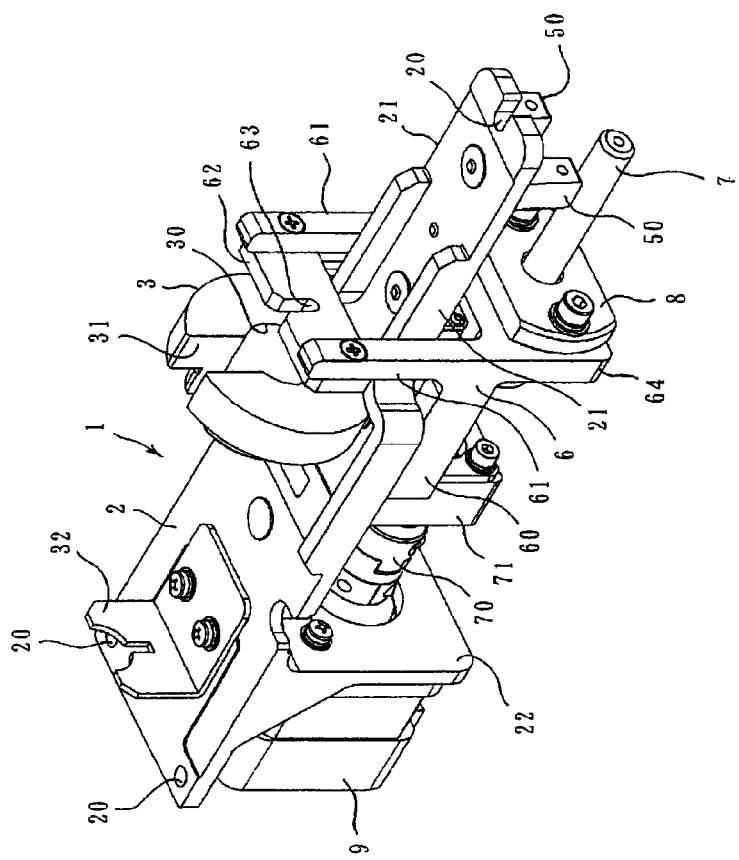
FIG. 1 A front-side perspective view illustrating an example of a syringe drive unit to which the present invention is applied.
Figure 2:
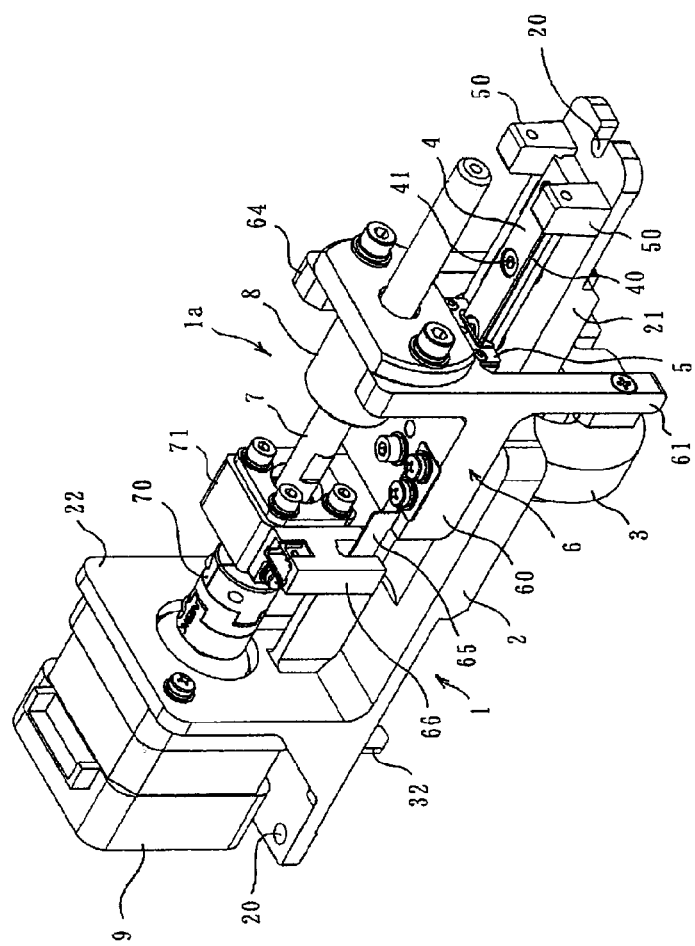
FIG. 2 A rear-side perspective view of the syringe drive unit illustrated in FIG. 1.
Figure 3:
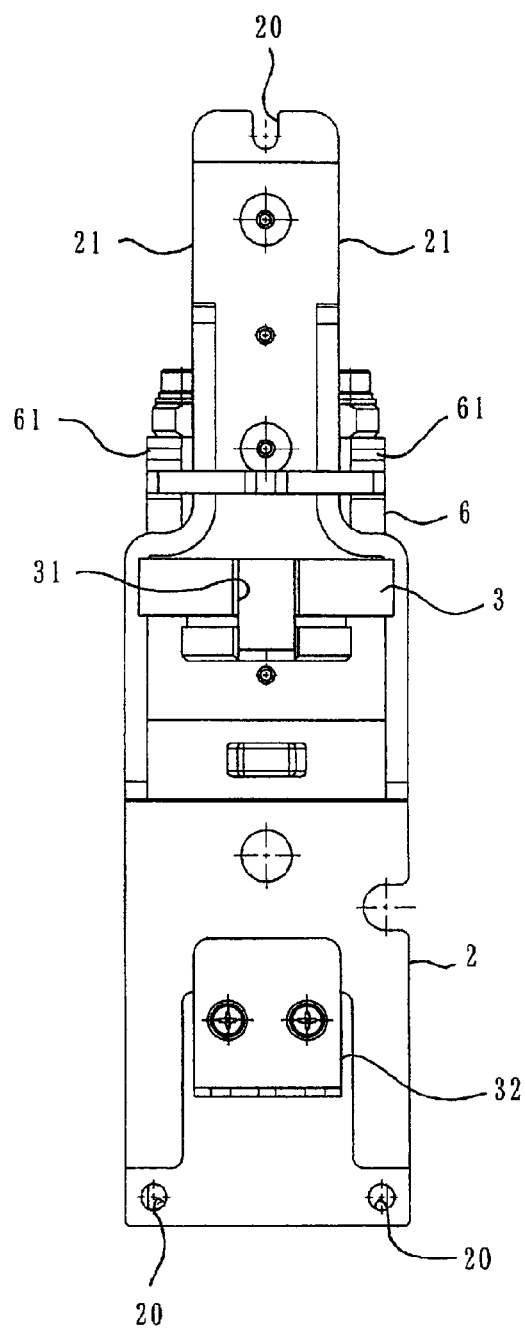
FIG. 3 A front view of the syringe drive unit illustrated in FIG. 1.
Figure 4:
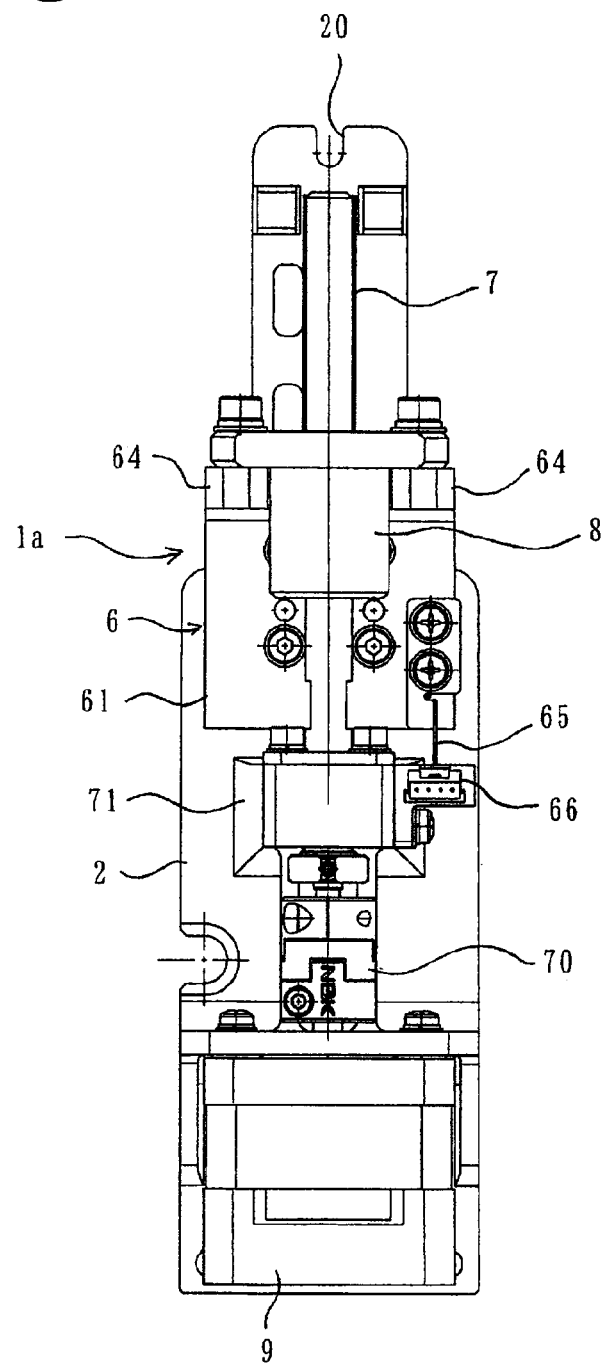
FIG. 4 A rear view of the syringe drive unit illustrated in FIG. 1.
Figure 5:
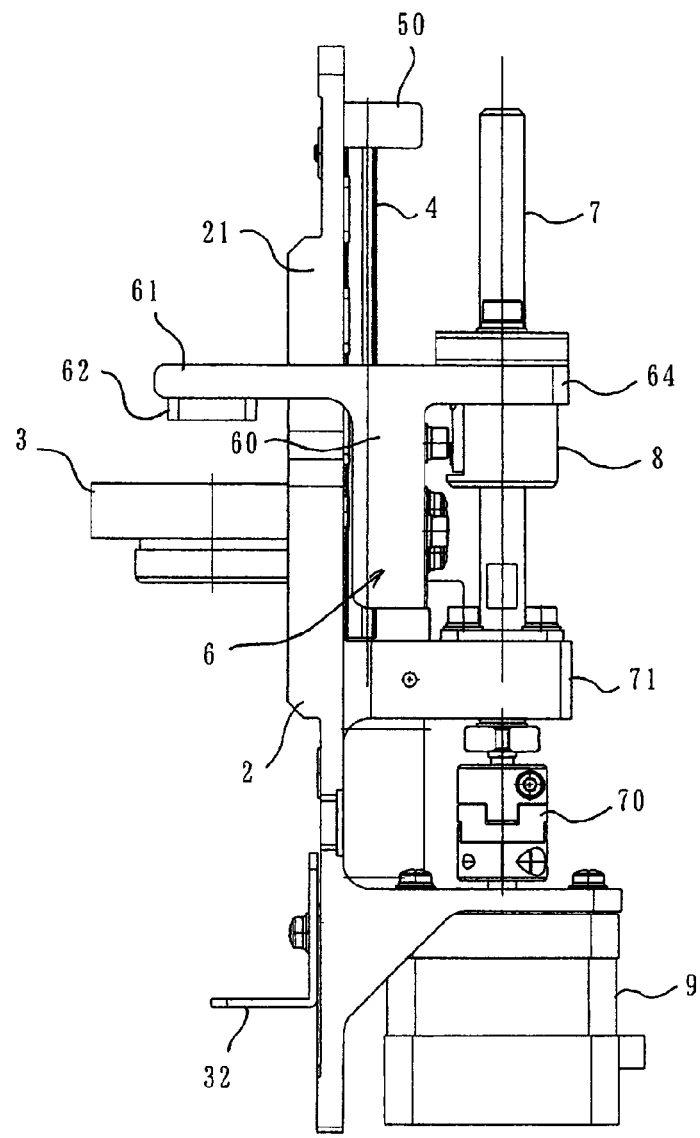
FIG. 5 A right side view of the syringe drive unit illustrated in FIG. 1.
Figure 6:
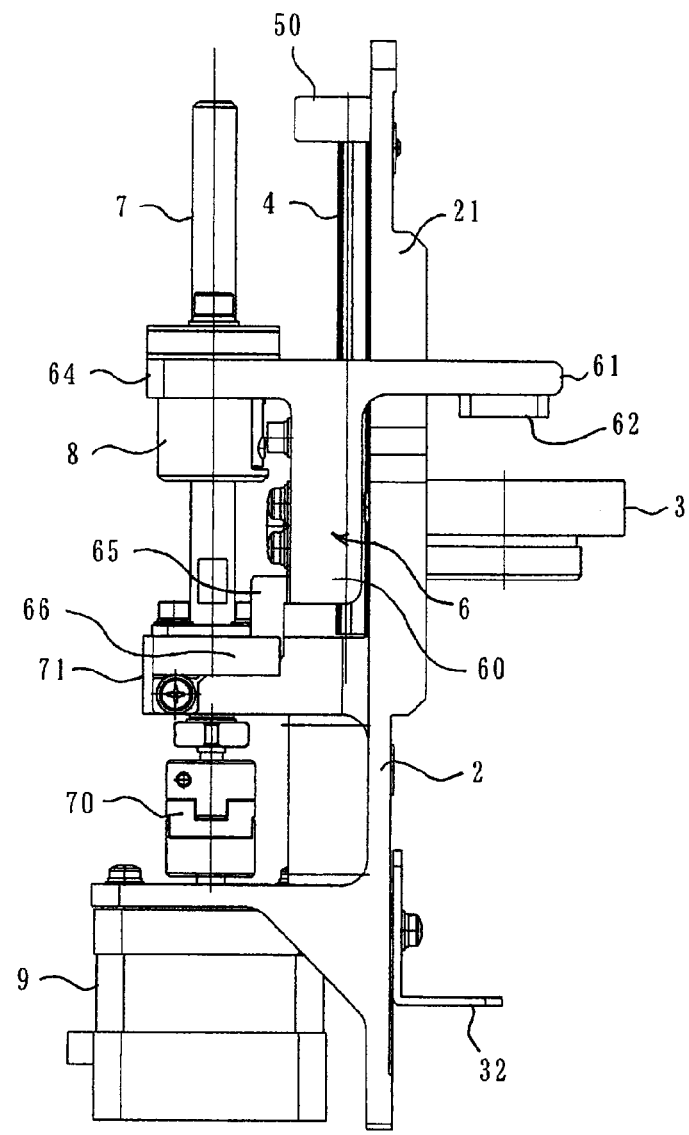
FIG. 6 A left side view of the syringe drive unit illustrated in FIG. 1.
Figure 7:
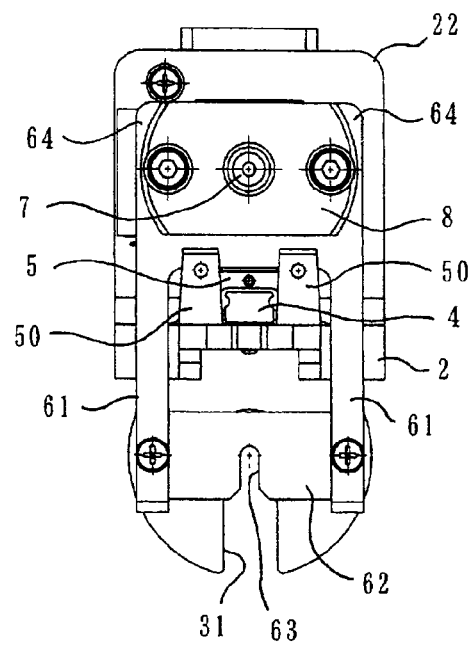
FIG. 7 A plan view of the syringe drive unit illustrated in FIG. 1.
Figure 8:
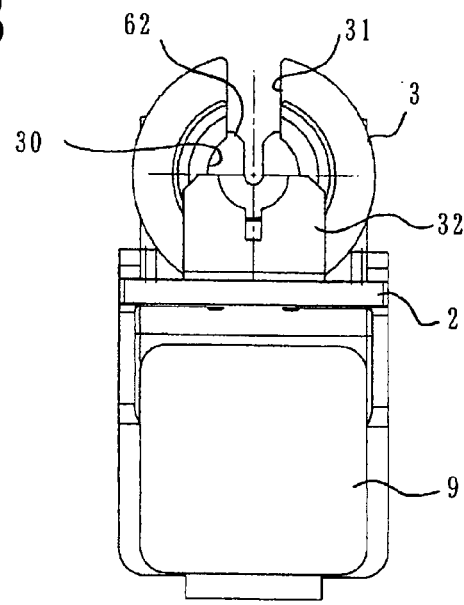
FIG. 8 A bottom view of the syringe drive unit illustrated in FIG. 1.

FIGS. 1 to 8 illustrate an embodiment of a syringe drive unit (hereinafter, referred to as "drive unit") to which the present invention is applied. A drive unit 1 is used with a syringe (not shown) mounted thereto, the syringe including a syringe body and a plunger, for the purpose of pushing the plunger into the syringe body at a predetermined speed and ejecting liquid medicine loaded into the syringe body at a predetermined flow rate.

In the drive unit 1, a front surface side of a base plate 2 serves as a syringe holding region, and a rear surface side of the base plate 2 serves as an arrangement region for a drive mechanism 1a for pressing the plunger. The base plate 2 is formed to be longitudinal in one direction, and the syringe is held on the base plate 2, with an axial line thereof conforming to the longitudinal direction. Structures are fixed respectively to a front surface and a rear surface of the base plate 2. Thus, both end portions of the base plate 2 are fixed to other apparatuses by a fixing method such as screwing, and fixing-bolt passing holes 20 are provided at the end portions of the base plate 2.

A syringe holder 3 for holding the syringe body is screwed on the front surface side of the base plate 2. The syringe holder 3 is provided with a holding hole 30 formed at a center thereof so that the syringe body is mounted. That is, the syringe holder 3 is formed in a substantially doughnut-like shape. A slit 31 to be used at the time of fitting of the syringe body into the holding hole 30 is provided along a radial direction. Further, in order to prevent the syringe body from moving into the axial-line direction, a flange portion of the syringe body fitted to the holding hole 30 is engaged with a periphery of the holding hole 30 of the syringe holder 3. Further, an auxiliary holder 32 for supporting a leading end portion of the syringe body is provided upright on the base plate 2, and cooperation of the syringe holder 3 and the auxiliary holder 32 enables the syringe body to be reliably held along the axial-line direction thereof, that is, a direction in which the plunger is pressed.

Meanwhile, the drive mechanism 1a for pressing the plunger is arranged on the rear surface side of the base plate 2. The drive mechanism 1a mainly includes a guide mechanism and a feed screw mechanism. The guide mechanism includes a guide rail 4 fixed to the base plate 2, a slider 5 assembled to the guide rail 4 and movable along the guide rail 4, and a plunger pressing member 6 fixed to the slider 5.

The guide rail 4 is formed into a substantially rectangular shape in cross-section perpendicular to the longitudinal direction, and rolling grooves 40 for balls are formed in both side surfaces of the guide rail 4. The guide rail 4 is fixed to the base plate 2 with a fixing bolt 41 in such a manner that the longitudinal direction thereof conforms to the axial-line direction of the syringe body held by the syringe holder 3. Further, the slider 5 is formed into a substantially saddle-like shape so as to stride over the guide rail 4, and assembled to the guide rail 4 through intermediation of a large number of balls which roll in the rolling grooves 40 of the guide rail 4. The slider 5 incorporates a ball infinite-circulation path, and hence is capable of moving, without limitation of strokes, on the guide rail 4 in a state of striding over the guide rail 4. Note that, in the figure, a stopper member for preventing overrun of the slider 5 with respect to the guide rail 4 is denoted by reference symbol 50.

Well-known linear guide devices may be arbitrarily selected and used as the guide rail 4 and the slider 5. In this case, shapes of the guide rail 4 and the slider 5 may be arbitrarily selected in accordance with a required bearing capacity. Similarly, rollers may be selected instead of the balls as rolling elements interposed between the guide rail 4 and the slider 5.

Further, the plunger pressing member 6 includes a fixed plate 60 fixed so as to be superimposed on the slider 5, a pair of arm portions 61 provided upright from the fixed plate 60 toward the base plate 2, and a flange portion 64 to which a nut member of the feed screw mechanism described below is fixed. The base plate 2 is provided with cutout portions 21 on both sides of an installation position of the guide rail 4. The arm portions 61 of the plunger pressing member 6 project from the rear surface side to the front surface side of the base plate 2 through the cutout portions 21 of the base plate 2, that is, to a region in which a syringe pump is held. Further, at leading ends of the pair of arm portions 61 projecting to the rear surface side of the base plate 2, a plate-like plunger holder 62 is fixed so as to couple those arm portions 61 to each other. At a center of the plunger holder 62, a holding slit 63 for fitting of a shaft of the plunger is formed by cutting-out.

Thus, when the plunger pressing member 6 moves along the guide rail 4 together with the slider 5, the plunger holder 62 moves in accordance therewith along the axial-line direction of the syringe body. In this way, the plunger fixed to the plunger holder 62 moves into the axial-line direction with respect to the syringe body.

Meanwhile, the feed screw mechanism includes a screw shaft 7 provided parallel to the guide rail 4 immediately above the guide rail 4, a nut member 8 threadedly engaged with the screw shaft 7, and a motor 9 for rotating the screw shaft 7.

The screw shaft 7 has an outer peripheral surface provided with a helical ball-rolling groove (not shown), and one end coupled to a rotary shaft of the motor 9 through intermediation of a coupling 70. Further, rotation of the screw shaft 7 is supported by a support block 71 provided on the base plate 2. Further, the motor 9 is a stepping motor, which is rotated by a predetermined angle in response to a pulse signal supplied from a driver circuit (not shown), and transmits the rotation to the screw shaft 7. The motor 9 is fixed to a motor fixing plate 22 provided upright on the base plate 2.

Further, the nut member 8 is threadedly engaged with the screw shaft 7 through intermediation of a large number of balls, and incorporates the ball infinite-circulation path. That is, the screw shaft 7 and the nut member 8 constitute a ball screw apparatus. The nut member 8 is fixed to the flange portion 64 provided upright from the plunger pressing member 6, and movable along the guide rail 4 into the axial direction of the screw shaft 7 together with the plunger pressing member 6. Thus, when the screw shaft 7 is rotated in accordance with the rotation of the motor 9, the nut member 8 moves into the axial direction of the screw shaft 7, that is, into the longitudinal direction of the guide rail 4, by a distance corresponding to a rotational amount of the screw shaft 7.

Note that, in the feed screw mechanism, it is not necessary for the nut member 8 and the screw shaft 7 to be threadedly engaged with each other through intermediation of the balls. Instead, it is possible to use a feed screw mechanism of such a type that the screw shaft 7 and the nut member 8 are held in sliding contact with each other. Further, as described in this embodiment with reference to FIGS. 1 to 8, the guide mechanism for operating the plunger pressing member 6 along a certain path and the feed screw mechanism for causing the plunger pressing member 6 to exert a pressing force are formed separately from each other. In this context, for example, the slider 5 of the guide mechanism and the nut member 8 of the feed screw mechanism may be integrated with each other so that the slider 5 of the guide mechanism is threadedly engaged with the screw shaft 7 directly. In addition, the guide rail 4 may be formed integrally with the base plate 2.

In the drive unit 1 in this embodiment, the moving amount of the plunger pressing member 6 is controlled by the number of pulse signals applied to the stepping motor 9. Thus, a position of the plunger pressing member 6 on the guide rail 4 can be grasped by counting the number of pulse signals. Note that, in order to prevent overrun of the slider 5 into a direction in which the plunger is pressed, a limit switch is provided between the plunger pressing member 6 and the base plate 2. The limit switch includes a plate-like detection trigger 65 which is fixed to the plunger pressing member 6, and a detection sensor 66 which is fixed to the base plate 2 and detects insertion of the detection trigger 65. When the plunger pressing member 6 moves in the direction in which the plunger is pressed and when the slider 5 comes close to an end portion of the guide rail 4, the detection trigger 65 is detected, by the detection sensor 66. In response to a signal output from the detection sensor 66, the driver circuit stops the motor 9.

In the drive unit 1 structured as described above, the syringe body of the syringe is mounted to the syringe holder. Meanwhile, when the plunger housed in the syringe body is mounted to the plunger holder 62 and the motor 9 is rotated in this state, the plunger pressing member 6 moves in the axial-line direction of the syringe body in accordance with the rotational amount of the motor 9, and the plunger holder 62 fixed to the arm portions 61 of the plunger pressing member 6 exerts a pressing force with respect to the plunger. As a result, the plunger is pushed into the syringe body.

In this case, the nut member 8 for propelling the plunger pressing member 6 and the plunger holder 62 for pressing the plunger are positioned separately from each other respectively on the front and rear of the base plate 2. Further, the plunger exerts a pressing reaction force with respect to the arm portions 61 of the plunger pressing member 6. Thus, a moment load acts on the plunger pressing member 6, and a posture of the plunger pressing member 6 is liable to be influenced by the moment load. However, in the drive unit 1, the guide rail 4 is installed with respect to the base plate 2, and the plunger pressing member 6 is fixed to the slider 5 assembled to the guide rail 4 through intermediation of the large number of balls. Thus, the plunger pressing member 6 can be moved against the moment load while maintaining a certain posture.

Thus, the moving amount of the nut member 8 in accordance with the rotational amount of the motor 9 can be accurately transmitted to the plunger pressing member 6. In addition, a pushing-in amount of the plunger with respect to the syringe body can be controlled with higher accuracy, with the result that liquid medicine can be ejected from the syringe body with high accuracy.

Further, the pair of arm portions 61 provided to the plunger pressing member 6 project through the cutout portions 21 of the base plate 2, which are provided on both sides, of the guide rail 4, from the rear surface side to the front surface side of the base plate 2, and the plunger is pressed by the plunger holder 62 provided so as to couple the pair of arm portions 61. Thus, the posture of the plunger holder 62 at the time of pressing the plunger is stabilized. Also in this regard, the pushing-in amount of the plunger with respect to the syringe body can be controlled with higher accuracy.

Further, the flange portion 64 of the plunger pressing member 6, to which the nut member 8 is fixed, is provided upright into a direction opposite to that of the arm portions 61 with respect to the fixed plate 60 of the plunger pressing member 6. Thus, in the drive unit 1, the plunger holder 62 fixed to the leading end of each of the arm portions 61 and the nut member 8 are positioned so as to sandwich the guide rail 4. In other words, the guide rail 4 is positioned between a point of action of a propulsive force for moving the plunger pressing member 6 and a point of action of a pressing force with respect to the plunger. Also in this regard, the slider 5 moving along the guide rail 4 is capable of guiding the plunger pressing member 6 with high accuracy.

Further, according to the drive unit 1, the front surface side of the base plate 2 serves as the syringe holding region, and the rear surface side thereof serves as the arrangement region for the drive mechanism 1*a*. Thus, even when the liquid medicine ejected from the syringe leaks out, the base plate 2 functions as a shield. Thus, there is no such risk that the liquid medicine drops onto the drive mechanism 1*a* positioned on the rear surface side of the base plate 2. Further, the base plate 2 separates the syringe holding region and the drive mechanism 1*a*. Thus, it is also possible to avoid such a risk that a user mistakenly touches the feed screw mechanism at the time of a mounting/removing operation of the syringe.

The invention claimed is:

1. A syringe drive unit, comprising:
   a base plate;
   a syringe holder which is fixed to a front surface side of the base plate and holds a syringe body;
   a guide rail which is provided on a rear surface side of the base plate along an axial-line direction of the syringe body mounted to the syringe holder;
   a slider which is assembled to the guide rail through intermediation of a large number of rolling elements and movable along the guide rail;
   a plunger pressing member which is fixed to the slider and comprises an arm portion projecting from the rear surface side of the base plate to the front surface side of the base plate, the arm portion holding a plunger housed in the syringe body;
   a screw shaft which is provided on the rear surface side of the base plate parallel to the guide rail and has predetermined rotation imparted by a motor; and
   a nut member which is threadedly engaged with the screw shaft to impart a moving amount corresponding to a rotation angle of the motor to the plunger pressing member,
   wherein the guide rail is formed into a substantially rectangular shape in cross-section perpendicular to a moving direction of the slider and installed on the base plate,
   wherein the slider is formed into a shape of a saddle striding over the guide rail,
   wherein the base plate is provided with cutout portions on both sides of an installation position of the guide rail,
   wherein the plunger pressing member comprises a fixed plate fixed to the slider, and
   wherein the arm portion comprises a pair of arm portions provided upright on the fixed plate and passing through the cutout portions of the base plate.

2. The syringe drive unit according to claim 1, wherein the plunger pressing member comprises a flange portion for fixing the nut member, the flange portion being provided upright from the fixed plate into a direction opposite to a direction of the pair of arm portions.

3. A syringe drive unit, comprising:
   a base plate;
   a syringe holder which is fixed to a front surface side of the base plate and holds a syringe body;

a guide rail which is provided on a rear surface side of the base plate along an axial-line direction of the syringe body mounted to the syringe holder;

a slider which is assembled to the guide rail through intermediation of a large number of rolling elements and movable along the guide rail;

a plunger pressing member which is fixed to the slider and comprises an arm portion projecting from the rear surface side of the base plate to the front surface side of the base plate, the arm portion holding a plunger housed in the syringe body;

a screw shaft which is provided on the rear surface side of the base plate parallel to the guide rail and has predetermined rotation imparted by a motor; and a nut member which is threadedly engaged with the screw shaft to impart a moving amount corresponding to a rotation angle of the motor to the plunger pressing member, wherein the plunger pressing member comprises a flange portion for fixing the nut member, the flange portion being provided upright from the fixed plate into a direction opposite to a direction of the pair of arm portions.

\* \* \* \* \*